(12) United States Patent
Shimizu

(10) Patent No.: US 8,680,302 B2
(45) Date of Patent: Mar. 25, 2014

(54) METHOD FOR PRODUCING ALCOHOL COMPOUND

(75) Inventor: Hideo Shimizu, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 302 days.

(21) Appl. No.: 13/126,289

(22) PCT Filed: Dec. 11, 2008

(86) PCT No.: PCT/JP2008/072540
§ 371 (c)(1),
(2), (4) Date: Apr. 27, 2011

(87) PCT Pub. No.: WO2010/067442
PCT Pub. Date: Jun. 17, 2010

(65) Prior Publication Data
US 2011/0201819 A1 Aug. 18, 2011

(51) Int. Cl.
*C07C 45/00* (2006.01)
*C07C 29/14* (2006.01)
*C07D 307/00* (2006.01)

(52) U.S. Cl.
USPC ............... 549/429; 568/454; 568/882

(58) Field of Classification Search
USPC ................ 549/429; 568/454, 882
See application file for complete search history.

(56) References Cited

U.S. PATENT DOCUMENTS

| 4,929,776 | A | 5/1990 | Grosselin et al. |
| 5,214,220 | A | 5/1993 | Drent |
| 5,763,688 | A | 6/1998 | Ikariya et al. |
| 2009/0203927 | A1 | 8/2009 | Shimizu et al. |
| 2010/0137615 | A1 | 6/2010 | Shimizu et al. |
| 2010/0168440 | A1 | 7/2010 | Shimizu et al. |
| 2011/0065929 | A1 | 3/2011 | Shimizu et al. |

FOREIGN PATENT DOCUMENTS

| JP | 02-000220 A | 1/1990 |
| JP | 05-246916 A | 9/1993 |
| JP | 08-225467 A | 9/1996 |
| WO | 2007/007646 A1 | 1/2007 |

OTHER PUBLICATIONS

Jian-Xin Chen, et al., "Highly Chemoselective Catalytic Hydrogenation of Unsaturated Ketones and Aldehydes to Unsaturated Alcohols Using Phosphine-Stabilized Copper (I) Hydride Complexes", Tetrahedron, 2000, pp. 2153-2166, vol. 56, No. 15.
Hideo Shimizu, et al., "Asymmetric Hydrogenation of Aryl Ketones Mediated by a Copper Catalyst", Organic Letters, 2007, pp. 1655-1657, vol. 9, No. 9.
Jian-Xin Chen, et al., "Phosphine Effects in the Copper (I) Hydride-Catalyzed Hydrogenation of Ketones and Regioselective 1,2-Reduction of $\alpha,\beta$-Unsaturated Ketones and Aldehydes. Hydrogenation of Decalin and Steroidal Ketones and Enones", Tetrahedron, 2000, pp. 2789-2798, vol. 56, No. 18.
P. Baumeister, et al., "Selective Hydrogenation of Functionalized Hydrocarbons", Organic Reactions, 1997, pp. 2186-2209, vol. 4.
Takashiro Muroi, "Industrial Noble Metal Catalyst", JETI, 2003, pp. 111-208.
Matthew L. Clarke, et al. "Homogeneous Hydrogenation of Aldehydes, Ketones, Imines and Carboxylic Acid Derivatives: Chemoselectivity and Catalytic Activity", The Handbook of Hydrogenations of Aldehydes, 2007, pp. 413-454, vol. 1.

*Primary Examiner* — Andrew D Kosar
*Assistant Examiner* — Raymond Covington
(74) *Attorney, Agent, or Firm* — Sughrue Mion, PLLC

(57) ABSTRACT

Disclosed is a practical method for efficiently producing an alcohol compound by hydrogenating an aldehyde by using a homogeneous copper catalyst which is an easily-available low-cost metal species. Specifically disclosed is a method for producing an alcohol compound, which is characterized in that a hydrogenation reaction of an aldehyde compound is performed in the presence of a homogeneous copper catalyst and a diphosphine compound.

2 Claims, No Drawings

METHOD FOR PRODUCING ALCOHOL COMPOUND

CROSS REFERENCE TO RELATED APPLICATIONS

This application is a National Stage of International Application No. PCT/JP2008/072540 filed Dec. 11, 2008, the contents of all of which are incorporated herein by reference in their entirety.

TECHNICAL FIELD

The present invention relates to a method for producing an alcohol compound, and more specifically to a method for producing an alcohol compound by performing a hydrogenation reaction of an aldehyde compound in the presence of a homogeneous copper catalyst and a diphosphine compound.

BACKGROUND ART

Conventionally, alcohol compounds have been widely used as components or synthetic intermediates and the like for various pharmaceuticals, agricultural chemicals, flavors, fragrances, or commodity chemicals. As methods for producing such alcohol compounds, methods by which an alcohol compound is obtained by hydrogenation of an aldehyde compound have been known to be useful methods. In this connection, various catalysts and reaction modes have been proposed for the hydrogenation reaction. A method by which, among aldehyde compounds, an α,β-unsaturated aldehyde is selectively hydrogenated to obtain an allyl alcohol is said to be particularly useful.

As methods for obtaining an alcohol compound by a heterogeneous catalyst reaction in which an aldehyde compound is hydrogenated, methods have been known which use an iridium catalyst, an osmium catalyst, a palladium catalyst, a nickel catalyst, a platinum catalyst, a ruthenium catalyst, or the like, as described in Non-Patent Document 1 and Non-Patent Document 2, for example. However, these methods often requires harsh reaction conditions such as high temperature or high pressure, and are severely limited in terms of operability, production apparatus, and the like. Moreover, particularly in the cases where an α,β-unsaturated aldehyde is used as the hydrogenation substrate, there is a problem that the selectivity is generally low.

Meanwhile, as methods for obtaining an alcohol compound by a homogeneous catalyst reaction in which an aldehyde compound is hydrogenated, methods which use a complex using a platinum group metal and other methods have been known (for example, see Non-Patent Document 3 and Patent Document 1). However, such a complex uses a platinum group metal, which is expensive. Hence, there are problems from the economical view point that the complex is expensive and that the influence of fluctuation of the price of a metal of interest is large. Moreover, there is a problem that, when an α,β-unsaturated aldehyde is used as the hydrogenation substrate, iridium complexes, rhodium complexes, and osmium complexes have low selectivity.

In recent years, a method has been reported in which an aldehyde is hydrogenated by use of a catalyst made of a copper compound and dimethylphenylphosphine (Non-Patent Document 4). However, there is a problem of operability because it is necessary to use dimethylphenylphosphine, which is unstable in the air, and highly smells, in an excessive amount with respect to copper. In addition, there also is a problem of cost effectiveness because the catalytic activity is low, and consequently it is necessary to use a large amount of the catalyst (2 to 5 mol % in terms of Cu). Meanwhile, in Non-Patent Document 4, a method is developed which uses $[(tripod)CuH]_2$ as the catalyst, also. However, the method has the following problem. Specifically, since the catalytic activity is extremely low, it is necessary to use a tridentate ligand Tripod in an excessive amount with respect to copper for the reaction to be completed, even when the catalyst is used at 2.5 mol % with respect to the substrate. In addition, there is a problem of operability because the range of pressure for the reaction to proceed is from 50 to 70 psi (approximately 0.35 to 0.5 MPa), which is extremely narrow.

Note that, in Patent Document 2 and Non-Patent Document 5, a catalyst for a homogeneous asymmetric hydrogenation reaction has been developed using a copper catalyst. However, this is a method for obtaining an optically active compound by hydrogenating a ketone moiety or a double bond of a prochiral unsaturated compound, and neither Patent Document 2 nor Non-Patent Document 5 describes hydrogenation of aldehydes.

Patent Document 1: Japanese Patent Application Publication No. Hei 08-225467
Patent Document 2: International Patent Application Publication No. WO2007/007646.
Non-Patent Document 1: Handbook of Heterogeneous Hydrogenation, Ertl, G.; Knozinger, H.; Weitkamp, J. Eds., VCH Weinheim, 1997, p. 2186.
Non-Patent Document 2: Muroi, Takashiro, "KOUGYOU KIKINZOKU SHOKUBAI (Industrial Noble Metal Catalyst)," 2003, p. 111.
Non-Patent Document 3: Handbook of Homogeneous Hydrogenation, de Vries, J. G.; Elsevier, C. J. Eds., Wiley-VCH Weinheim, 2007, Vol. 1. p. 413.
Non-Patent Document 4: Chen, J.-X.; Daeuble, J. F.; Bresdensky, D. M.; Stryker, J. M. Tetrahedron 2000, 56, 2153.
Non-Patent Document 5: Shimizu, H.; Igarashi, D.; Kuriyama, W.; Yusa, Y.; Sayo, N.; Saito, T. Org. Lett. 2007, 9, 1655.

DISCLOSURE OF THE INVENTION

Problem to be Solved by the Invention

An object of the present invention is to provide a practical method for efficiently producing an alcohol compound by hydrogenating an aldehyde by using a homogeneous copper catalyst which is an easily-available low-cost metal species.

Means for Solving the Problem

In view of the above described circumstances, the present inventor has conducted earnest study. As a result, the present inventor has found a method for producing an alcohol compound at a high yield and at a high catalytic efficiency, by performing a hydrogenation reaction of an aldehyde compound in the presence of a homogeneous copper catalyst and a diphosphine compound. This finding has led to the completion of the present invention.

Specifically, the present invention provides a method for producing an alcohol compound, characterized by performing a hydrogenation reaction of an aldehyde compound in the presence of a homogeneous copper catalyst and a diphosphine compound.

Note that, in the present invention, "homogeneous" means a state where the catalyst used is substantially dissolved during the hydrogenation reaction, and a state where the catalyst used is dissolved or dissolvable during the hydrogenation reaction. The "homogeneous" means a state where the catalyst is dissolved depending on the kinds of a hydrogenation substrate and a solvent used, the reaction conditions such as reaction temperature, and the like. This state, for example, includes a case where the catalyst used is dissolved with the increase of the reaction temperature, and similar cases. Moreover, the "homogeneous" means a case where characteristics of the reaction system hardly change at the interface, and are uniform over the entirety, that is, a state where the catalyst having a catalyst activity in the reaction system is dissolved or dissolvable in a solution, where the hydrogenation substrate used for the homogeneous hydrogenation reaction, an additive used if necessary, a deactivated catalyst, or the like may be present as solid.

Effects of the Invention

According to the production method of the present invention, it is possible to produce an alcohol compound from an aldehyde compound at a high yield and at a high catalytic efficiency.

BEST MODES FOR CARRYING OUT THE INVENTION

Hereinafter, the present invention will be described in detail.

A method for producing an alcohol compound of the present invention is characterized by performing a hydrogenation reaction of an aldehyde compound in the presence of a homogeneous copper catalyst and a diphosphine compound.

In the present invention, an aldehyde compound is used as a hydrogenation substrate, which is a raw material. As the aldehyde compound used as the hydrogenation substrate, various kinds of aldehydes can be used. For example, those represented by the following general formula (2) and the like can be used as appropriate:

$$R\text{---}CHO \quad (2)$$

(where R represents an aryl group which may have a substituent, a heterocyclic group which may have a substituent, or a saturated or unsaturated, chain or cyclic hydrocarbon group which may have a substituent).

Examples of the aryl group represented by R in the formula (2) include aromatic monocyclic and aromatic polycyclic groups such as a phenyl group, a naphthyl group, an anthryl groups, a phenanthryl group, and an indenyl group. Moreover, the examples also include metallocenyl groups such as a ferrocenyl group.

Examples of the heterocyclic group represented by R in the formula (2) include heteromonocyclic or heteropolycyclic groups such as a furyl group, a thienyl group, a pyridyl group, a pyrimidinyl group, a pyrazinyl group, a pyridazinyl group, a pyrazolyl group, an imidazolyl group, an oxazolyl group, a thiazolyl group, a benzofuryl group, a benzothienyl group, a quinolyl group, an isoquinolyl group, a quinoxalinyl group, a phthalazinyl group, a quinazolinyl group, a naphthyridinyl group, a cinnolinyl group, a benzoimidazolyl group, a benzoxazolyl group, and a benzothiazolyl group.

Examples of the saturated or unsaturated, chain or cyclic hydrocarbon group represented by R in the formula (2) include alkyl groups such as a methyl group, an ethyl group, a n-propyl group, an isopropyl group, a n-butyl group, an isobutyl group, a s-butyl group, a t-butyl group, a pentyl group, a hexyl group, a heptyl group, and an octyl group; cycloalkyl groups such as a cyclopropyl group, a cyclobutyl group, a cyclopentyl group, and a cyclohexyl group; and groups of unsaturated hydrocarbons and the like, such as a benzyl group, a vinyl group, and a methallyl group.

Here, each of the aryl group, the heterocyclic group, and the hydrocarbon group may have a substituent. Examples of the substituent include alkyl groups, alkenyl groups, aryl groups, alaryl groups, alicyclic groups, halogen atoms, a hydroxy group, alkoxy groups, a carboxyl group, ester groups, an amino group, dialkylamino groups, heterocyclic groups, and the like.

Here, examples of the alkyl group as the substituent include linear or branched alkyl groups having, for example, 1 to 15 carbon atoms, preferably 1 to 10 carbon atoms, and more preferably 1 to 6 carbon atoms. Specific examples thereof include a methyl group, an ethyl group, a n-propyl group, an isopropyl group, a n-butyl group, a s-butyl group, an isobutyl group, a t-butyl group, a n-pentyl group, a neopentyl group, a n-hexyl group, and the like.

Examples of the alkenyl group as the substituent include alkenyl groups having, for example, 2 to 10 carbon atoms, and specific examples thereof include a vinyl group, a 2-propenyl group, and the like.

Examples of the aryl group as the substituent include aryl groups having, for example, 6 to 14 carbon atoms, and specific examples thereof include a phenyl group, a naphthyl group, an anthryl group, a phenanthryl group, a biphenyl group, and the like.

Examples of the alaryl group as the substituent include a benzyl group, a 1-phenylethyl group, and the like.

Examples of the alicyclic group as the substituent include cycloalkyl groups having 5 to 8 carbon atoms such as a cyclopentyl group, a cyclohexyl group, a cycloheptyl group, and a cyclooctyl group.

Examples of the halogen atom as the substituent include a fluorine atom, a chlorine atom, a bromine atom, and an iodine atom.

Examples of the alkoxy group as the substituent include linear or branched alkoxy groups having, for example, 1 to 6 carbon atoms, and specific examples thereof include a methoxy group, an ethoxy group, a n-propoxy group, an isopropoxy group, a n-butoxy group, a s-butoxy group, an isobutoxy group, a t-butoxy group, a n-pentyloxy group, a neopentyloxy group, a n-hexyloxy group, and the like.

Examples of the ester group as the substituent include alkyloxy carbonyl groups having 2 to 6 carbon atoms such as a methoxycarbonyl group and an ethoxycarbonyl group; aryloxy carbonyl groups having 6 to 10 carbon atoms such as a phenoxycarbonyl group; and the like.

Examples of the dialkylamino group as the substituent include a dimethyl amino group, a diethylamino group, and the like.

Examples of the heterocyclic group as the substituent include aliphatic heterocyclic groups and aromatic heterocyclic groups. Examples of the aliphatic heterocyclic groups include 5- to 8-membered, preferably 5- or 6-membered, monocyclic, polycyclic, or fused polycyclic aliphatic heterocyclic groups which have, for example, 2 to 14 carbon atoms, and which contain, as their hetero atoms, at least one, preferably 1 to 3 hetero atoms such as nitrogen atoms, oxygen atoms, and sulfur atoms. Specific examples of the aliphatic heterocyclic groups include a 2-oxopyrrolidyl group, a piperidino group, a piperazinyl group, a morpholino group, a tetrahydrofuryl group, a tetrahydropyranyl group, a tetrahydrothienyl group, and the like. Meanwhile, examples of the aromatic heterocyclic groups include 5- to 8-membered, preferably 5- or 6-membered, monocyclic, polycyclic, or fused polycyclic aromatic heterocyclic (heteroaryl) groups which have, for example, 2 to 15 carbon atoms, and which contain, as their hetero atoms, at least one, preferably 1 to 3 hetero atoms such as nitrogen atoms, oxygen atoms, and sulfur atoms. Specific examples of the aromatic heterocyclic groups include a furyl group, a thienyl group, a pyridyl group, a pyrimidinyl group, a pyrazinyl group, a pyridazinyl group, a pyrazolyl group, an imidazolyl group, an oxazolyl group, a thiazolyl group, a benzofuryl group, a benzothienyl group, a quinolyl group, an isoquinolyl group, a quinoxalyl group, a phthalazinyl group, a quinazolinyl group, a naphthyridinyl group, a cinnolinyl group, a benzoimidazolyl group, a benzoxazolyl group, a benzothiazolyl group, and the like.

These substituents may be substituted with another substituent.

In addition, when R in the aldehyde compound used in the present invention is an unsaturated hydrocarbon group, i.e., when, for example, an α,β-unsaturated aldehyde compound represented by a general formula (3) is used as appropriate, the α,β-unsaturated aldehyde can be selectively hydrogenated, so that the corresponding allyl alcohol can be obtained:

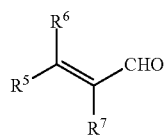

(3)

(where $R^5$ to $R^7$ each independently represent a hydrogen atom, an alkyl group which has 1 to 10 carbon atoms and which may have a substituent, an alicyclic group which has 5 to 8 carbon atoms and which may have a substituent, an alkenyl group which may have a substituent, an aryl group which may have a substituent, or a heterocyclic group which may have a substituent; and $R^5$ and $R^6$, as well as $R^5$ and $R^7$, may be bonded to each other to form a ring).

Examples of the alkyl group having 1 to 10 carbon atoms and represented by $R^5$ to $R^7$ in the formula (3) include alkyl groups having 1 to 10 carbon atoms such as a methyl group, an ethyl group, a n-propyl group, an isopropyl group, a n-butyl group, an isobutyl group, a s-butyl group, a t-butyl group, a pentyl group, a hexyl group, a heptyl group, an octyl group, a nonyl group, and a decyl group.

Examples of the alicyclic group having 5 to 8 carbon atoms and represented by $R^5$ to $R^7$ in the formula (3) include cycloalkyl groups having 5 to 8 carbon atoms such as a cyclopentyl group, a cyclohexyl group, a cycloheptyl group, and a cyclooctyl group.

Examples of the alkenyl group represented by $R^5$ to $R^7$ in the formula (3) include a vinyl group, a 2-propenyl group, and the like.

Examples of the aryl group represented by $R^5$ to $R^7$ in the formula (3) include aromatic monocyclic or aromatic polycyclic groups such as a phenyl group, a naphthyl group, an anthryl group, a phenanthryl group, and an indenyl group. The examples also include metallocenyl groups such as a ferrocenyl group.

Examples of the heterocyclic group represented by $R^5$ to $R^7$ in the formula (3) include heteromonocyclic or heteropolycyclic groups such as a furyl group, a thienyl group, a pyridyl group, a pyrimidinyl group, a pyrazinyl group, a pyridazinyl group, a pyrazolyl group, an imidazolyl group, an oxazolyl group, a thiazolyl group, a benzofuryl group, a benzothienyl group, a quinolyl group, an isoquinolyl group, a quinoxalinyl group, a phthalazinyl group, a quinazolinyl group, a naphthyridinyl group, a cinnolinyl group, a benzoimidazolyl group, a benzoxazolyl group, and a benzothiazolyl group.

Here, each of the alkyl groups, the alicyclic groups, the alkenyl groups, the aryl groups, and the heterocyclic groups may have a substituent. Examples of the substituent include alkyl groups, alkenyl groups, aryl groups, alaryl groups, alicyclic groups, halogen atoms, a hydroxy group, alkoxy groups, a carboxyl group, ester groups, an amino group, dialkylamino groups, heterocyclic groups, and the like.

Here, the substituent is the same as that described for R in the general formula (2).

Meanwhile, when $R^5$ and $R^6$, or $R^5$ and $R^7$ are bonded to each other to form a ring, examples of the ring include those in which $R^5$ and $R^6$ together form an alkylene group having 4 to 6 carbon atoms such as a tetramethylene group, a pentamethylene group, and a hexamethylene group; and those in which $R^5$ and $R^7$ together form an alkylene group having 3 to 5 carbon atoms such as a trimethylene group, a tetramethylene group, and a pentamethylene group.

In the present invention, when R is an aryl group which may have a substituent or a heterocyclic group which may have a substituent, specific examples of the aldehyde compound of the above-described general formula (2) include benzaldehyde, p-tolylaldehyde, cuminaldehyde, salicylaldehyde, anisaldehyde, o-methoxy benzaldehyde, o-methoxy cinnamic aldehyde, vanillin, ethyl vanillin, 3,4-dimethoxybenzaldehyde, piperonal, helional, phenoxyacetaldehyde, p-methylphenoxyacetaldehyde, furfural, 5-methylfurfural, 5-hydroxymethylfurfural, pyridinecarboxaldehyde, thiophenecarboxaldehyde, and the like.

Meanwhile, in the present invention, when R is a saturated or unsaturated, chain or cyclic hydrocarbon group, specific examples of the aldehyde compound of the general formula (2) include acetaldehyde, propionaldehyde, n-valeraldehyde, isovaleraldehyde, 2-methylbutanal, n-hexanal, n-heptanal, n-octanal, n-nonanal, 2-methyloctanal, 3,5,5-trimethylhexanal, decanal, undecanal, 2-methyldecanal, dodecanal, 2-methylundecanal, tridecanal, tetradecanal, citronellal, caryophyllene aldehyde, phenylacetaldehyde, p-methylphenylacetaldehyde, p-isopropylphenylacetaldehyde, hydratropaldehyde, p-methylhydratropaldehyde, phenylpropionaldehyde, 3-methyl-5-phenylvaleraldehyde, phenoxyacetaldehyde, p-methylphenoxyacetaldehyde, β-methylhydrocinnamic aldehyde, cyclamen aldehyde, p-ethyldimethylhydrocinnamic aldehyde, p-isobutyl-α-dimethylhydrocinnamic aldehyde, p-tert-butyl-α-dimethylhydrocinnamic aldehyde, and the like.

Moreover, in the present invention, specific examples of the α,β-unsaturated aldehyde compound of the general formula (3) include crotonaldehyde, β-methylcrotonaldehyde, 2-pentenal, trans-2-hexenal, trans-2-heptenal, trans-2-octenal, trans-2-nonenal, trans-2-decenal, trans-2-undecenal, trans-2-tridecenal, 2,4-hexadienal, 2,4-heptadienal, 2,4-octadienal, 2,4-nonadienal, 2,6-nonadienal, 2,4-decadienal, trimethyldecadienal, citral, geranial, neral, perillaldehyde, safranal, myrtenal, cinnamic aldehyde, α-methyl cinnamic aldehyde, 4-methyl-2-phenyl-2-pentenal, 5-methyl-2-phenyl-2-hexenal, α-amyl cinnamic aldehyde, α-hexyl cinnamic aldehyde, o-methoxy cinnamic aldehyde, β-phenyl cinnamic aldehyde, furylacrolein, and the like.

In the present invention, a homogeneous copper catalyst is used in the reaction system. The homogeneous copper catalyst is not particularly limited, as long as the reduction reaction of the present invention proceeds. For example, a homogeneous copper catalyst which can be represented by the following general formula (4) can be used:

$$[Cu(X)_l(L)_m]_n \qquad (4)$$

(where X represents a hydrogen atom, a halogen atom, an alkyl group, an aryl group, an alkoxy group, a carboxyl group, a triflate group, a nitrile group, dimethylformamide, $NO_3$, $SO_4$, $CO_3$, $BF_4$, or $BH_4$; L represents a monophosphine ligand; l represents an integer of 1 or 2; m represents 0 to 3; and n represents a natural number).

Examples of the halogen atom represented by X in the general formula (4) include a fluorine atom, a chlorine atom, a bromine atom, and an iodine atom.

Examples of the alkyl group represented by X in the general formula (4) include alkyl groups such as a methyl group, an ethyl group, a n-propyl group, an isopropyl group, a n-butyl group, an isobutyl group, a s-butyl group, a t-butyl group, a pentyl group, a hexyl group, a heptyl group, and an octyl group.

Examples of the aryl group of X in the general formula (4) include aromatic monocyclic or aromatic polycyclic groups such as a phenyl group, a naphthyl group, an anthryl group, a phenanthryl group, an indenyl group, and a mesityl group; and the like.

Examples of the alkoxy group represented by X in the general formula (4) include a methoxy group, an ethoxy group, a propoxy group, an isopropoxy group, a n-butoxy group, a t-butoxy group, a phenoxy group, a benzyloxy group, and the like.

Examples of the carboxyl group represented by X in the general formula (4) include a formyloxy group, an acetoxy group, a propionyloxy group, a butyryloxy group, a benzoyloxy group, and the like.

The monophosphine compound represented by L in the general formula (4) can be represented by the following general formula (5):

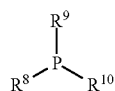

(5)

(where $R^8$ to $R^{10}$ each independently represent an alkyl group having 1 to 10 carbon atoms, an alicyclic group which has 5 to 8 carbon atoms and which may have a substituent, an aryl group which may have a substituent, or a heterocyclic group which may have a substituent; and any two of $R^8$, $R^9$, and $R^{10}$ may be bonded to each other to form a ring).

Examples of the alkyl group having 1 to 10 carbon atoms and represented by $R^8$ to $R^{10}$ in the general formula (5) include linear or branched alkyl groups having 1 to 10 carbon atoms, and examples thereof include a methyl group, an ethyl group, a n-propyl group, an isopropyl group, a n-butyl group, an isobutyl group, a s-butyl group, a t-butyl group, a n-pentyl group, a n-hexyl group, a n-octyl group, and the like.

Examples of the alicyclic group having 5 to 8 carbon atoms and represented by $R^8$ to $R^{10}$ in the general formula (5) include a cyclopentyl group, a cyclohexyl group, a cycloheptyl group, and the like.

Examples of the aryl group represented by $R^8$ to $R^{10}$ in the general formula (5) include aryl groups having 6 to 14 carbon atoms, and specific examples thereof include a phenyl group, a naphthyl group, an anthryl group, a phenanthryl group, a biphenyl group, and the like. Moreover, the examples also include metallocenyl groups such as a ferrocenyl group.

Examples of the heterocyclic group represented by $R^8$ to $R^{10}$ in the general formula (5) include heteromonocyclic or heteropolycyclic groups such as a furyl group, a thienyl group, a pyridyl group, a pyrimidinyl group, a pyrazinyl group, a pyridazinyl group, a pyrazolyl group, an imidazolyl group, an oxazolyl group, a thiazolyl group, a benzofuryl group, a benzothienyl group, a quinolyl group, an isoquinolyl group, a quinoxalinyl group, a phthalazinyl group, a quinazolinyl group, a naphthyridinyl group, a cinnolinyl group, a benzoimidazolyl group, a benzoxazolyl group, and a benzothiazolyl group.

Each of the alicyclic group having 5 to 8 carbon atoms, the aryl groups, and the heterocyclic groups represented by $R^8$ to $R^{10}$ in the general formula (5) may have a substituent. Examples of the substituent include alkyl groups, alkoxy groups, aryl groups, heterocyclic groups, and the like.

Here, examples of the alkyl group as the substituent include linear or branched alkyl groups having, for example, 1 to 15 carbon atoms, preferably 1 to 10 carbon atoms, and more preferably 1 to 6 carbon atoms, and specific examples thereof include a methyl group, an ethyl group, a n-propyl group, an isopropyl group, a n-butyl group, a s-butyl group, an isobutyl group, a t-butyl group, a n-pentyl group, a neopentyl group, a n-hexyl group, and the like.

Examples of the alkoxy group as the substituent include linear or branched alkoxy groups having, for example, 1 to 6 carbon atoms, and specific examples thereof include a methoxy group, an ethoxy group, a n-propoxy group, an isopropoxy group, a n-butoxy group, a s-butoxy group, an isobutoxy group, a t-butoxy group, a n-pentyloxy group, a neopentyloxy group, a n-hexyloxy group, and the like.

Examples of the aryl group as the substituent include aryl groups having, for example, 6 to 14 carbon atoms, and specific examples thereof include a phenyl group, a naphthyl group, an anthryl group, a phenanthryl group, a biphenyl group, and the like.

Examples of the heterocyclic group as the substituent include aliphatic heterocyclic groups and aromatic heterocyclic groups. Examples of the aliphatic heterocyclic groups include 5- to 8-membered, preferably 5- or 6-membered monocyclic, polycyclic, or fused polycyclic aliphatic heterocyclic groups which have, for example, 2 to 14 carbon atoms, and which contain, as their hetero atoms, at least one, preferably 1 to 3 hetero atoms such as nitrogen atoms, oxygen atoms, and sulfur atoms. Specific examples of the aliphatic heterocyclic groups include a 2-oxopyrrolidyl group, a piperidino group, a piperazinyl group, a morpholino group, a tetrahydrofuryl group, a tetrahydropyranyl group, a tetrahydrothienyl group, and the like. Meanwhile, examples of the aromatic heterocyclic groups include 5- to 8-membered, preferably 5- or 6-membered, monocyclic, polycyclic, or fused polycyclic aromatic heterocyclic (heteroaryl) groups which have, for example, 2 to 15 carbon atoms, and which contains, as their hetero atoms, at least one, preferably 1 to 3 hetero atoms such as nitrogen atoms, oxygen atoms, and sulfur atoms. Specific examples of the aromatic heterocyclic groups include a furyl group, a thienyl group, a pyridyl group, a pyrimidinyl group, a pyrazinyl group, a pyridazinyl group, a pyrazolyl group, an imidazolyl group, an oxazolyl group, a thiazolyl group, a benzofuryl group, a benzothienyl group, a quinolyl group, an isoquinolyl group, a quinoxalyl group, a phthalazinyl group, a quinazolinyl group, a naphthyridinyl group, a cinnolinyl group, a benzoimidazolyl group, a benzoxazolyl group, a benzothiazolyl group, and the like.

When any two of $R^8$, $R^9$, and $R^{10}$ are bonded to each other to form a ring, the ring formed by $R^8$ and $R^9$, $R^9$ and $R^{10}$, or $R^{10}$ and $R^8$, together with the phosphorus atom to which $R^8$, $R^9$, and $R^{10}$ are bonded may be a four-membered ring, a five-membered ring, or a six-membered ring. Specific examples of the ring include a phosphetane ring, a phospholane ring, a phosphorinane ring, a 2,4-dimethylphosphetane ring, a 2,4-diethylphosphetane ring, a 2,5-dimethylphospholane ring, a 2,5-diethylphospholane ring, a 2,6-dimethylphosphorinane ring, a 2,6-diethylphosphorinane ring, and the like.

Examples of the monophosphine compound represented by the general formula (5) include trimethylphosphine, triethylphosphine, tributylphosphine, triphenylphosphine, tritolylphosphine, tri(3,5-xylyl)phosphine, methyldiphenylphosphine, dimethylphenylphosphine, phenylphosphorane, and the like.

In addition, the homogeneous copper catalyst represented by the general formula (4) may contain a solvent of crystallization, if needed. Examples of the solvent of crystallization include water, methanol, ethanol, toluene, and the like.

Specific examples of the homogeneous copper catalyst represented by the general formula (4) in the cases where no monophosphine compound is coordinated to the complex include $CuF_2$, CuCl, $CuCl_2$, CuBr, $CuBr_2$, CuI, $CuI_2$, CuOTf, $Cu(OTf)_2$, $CuNO_3$, $Cu(NO_3)_2$, and the like.

Meanwhile, specific examples of the homogeneous copper catalyst represented by the general formula (4) in the cases where monophosphine compounds are coordinated to the complex include $[CuH(PPh_3)]_6$, $[Cu\ (NO_3)\ (PPh_3)_2]$, $[Cu(NO_3)(P(3,5-xyl)_3)_2]$, $[CuCl(PPh_3)_3]$, $[CuF(PPh_3)_3]\cdot 2EtOH$, $[Cu(O\text{-}t\text{-}Bu)(PPh_3)_2]$, $[Cu(OMs)(PPh_3)_2]$, $[Cu(BH_4)(PPh_3)_2]$, and the like.

In the description above, OTf represents a triflate group, xyl represents a xylyl group, and OMs represents a mesylate group.

Moreover, other specific examples of the homogeneous copper catalyst represented by the general formula (4) include homogeneous copper catalysts described in Reichle, W. T., Inorg. Chim. Acta, 1971, 5, p. 325, and the like.

These homogeneous copper catalysts may be used alone or in an appropriate combination with two or more kinds.

As the homogeneous copper catalyst, a commercially available product may be used. Alternatively, as a homogeneous copper catalyst in which a monophosphine compound is coordinated to the complex, one produced as appropriate by a publicly known method may be used. For example, the homogeneous copper catalyst may be prepared by the method described in "JIKKEN KAGAKU KOZA (Encyclopedia of Experimental Chemistry), fourth edition," vol. 18, (organometallic complexes), edited by the Chemical Society of Japan. For example, the homogeneous copper catalyst can be obtained by a reaction of a monophosphine compound with $CuX$, $CuX_2$, or a hydrate thereof (X has the same meaning as that of X in the general formula (4)).

Moreover, the homogeneous copper catalyst may be prepared by substitution of a homogeneous copper catalyst with a different substituent.

Note that the above-described homogeneous copper catalyst may be prepared in the reaction system at the time of the hydrogenation reaction of the present invention.

In the present invention, the amount of the catalyst used varies depending on a hydrogenation substrate, which is a raw material, reaction conditions, the kind of the catalyst, and the like, as well as cost effectiveness. However, the amount is generally in the range from 0.001 mol % to 10 mol %, preferably 0.01 mol % to 2 mol %, in terms of molar ratio of the homogeneous copper catalyst to the hydrogenation substrate.

In the present invention, a diphosphine compound is used in the reaction system. For example, the diphosphine compound can be represented by the following general formula (1):

(where $R^1$ to $R^4$ each independently represent an alkyl group having 1 to 10 carbon atoms, an alicyclic group which has 5 to 8 carbon atoms and which may have a substituent, an aryl group which may have a substituent, or a heterocyclic group which may have a substituent; $R^1$ and $R^2$, as well as $R^3$ and $R^4$, may be bonded to each other to form a ring; and A represents an alkylene chain which may have a substituent, a cycloalkanediyl group which may have a substituent, an alaryldiyl group which may have a substituent, or an aryldiyl group which may have a substituent).

Examples of the alkyl group having 1 to 10 carbon atoms and represented by $R^1$, $R^2$, $R^3$, or $R^4$ of the general formula (1) include a linear or branched alkyl groups having 1 to 10 carbon atoms, and examples thereof include a methyl group, an ethyl group, a n-propyl group, an isopropyl group, a n-butyl group, an-isobutyl group, a s-butyl group, a t-butyl group, a n-pentyl group, a n-hexyl group, a n-octyl group, and the like.

Examples of the alicyclic group having 5 to 8 carbon atoms and represented by $R^1$, $R^2$, $R^3$, or $R^4$ of the general formula (1) include a cyclopentyl group, a cyclohexyl group, a cycloheptyl group, and the like.

Examples of the aryl group represented by $R^1$, $R^2$, $R^3$, or $R^4$ of the general formula (1) include aryl groups having 6 to 14 carbon atoms, and specific examples thereof include a phenyl group, a naphthyl group, an anthryl group, a phenanthryl group, a biphenyl group, and the like. Moreover, the examples also include metallocenyl groups such as a ferrocenyl group.

Examples of the heterocyclic group represented by $R^1$, $R^2$, $R^3$, or $R^4$ of the general formula (1) include heteromonocyclic or heteropolycyclic groups such as a furyl group, a thienyl group, a pyridyl group, a pyrimidinyl group, a pyrazinyl group, a pyridazinyl group, a pyrazolyl group, an imidazolyl group, an oxazolyl group, a thiazolyl group, a benzofuryl group, a benzothienyl group, a quinolyl group, an isoquinolyl group, a quinoxalinyl group, a phthalazinyl group, a quinazolinyl group, a naphthyridinyl group, a cinnolinyl group, a benzoimidazolyl group, a benzoxazolyl group, and a benzothiazolyl group.

Each of the alicyclic group having 5 to 8 carbon atoms, the aryl group, and the heterocyclic group represented by $R^1$, $R^2$, $R^3$, or $R^4$ of the general formula (1) may have a substituent. Examples of the substituent include alkyl groups, alkoxy groups, aryl groups, heterocyclic groups, and the like.

Here, examples of the alkyl group as the substituent include linear or branched alkyl groups having, for example, 1 to 15 carbon atoms, preferably 1 to 10 carbon atoms, and more preferably 1 to 6 carbon atoms, and specific examples thereof include a methyl group, an ethyl group, a n-propyl group, an isopropyl group, a n-butyl group, a s-butyl group, an isobutyl group, a t-butyl group, a n-pentyl group, a neopentyl group, a n-hexyl group, and the like.

Examples of the alkoxy group as the substituent include linear or branched alkoxy groups having, for example, 1 to 6 carbon atoms, and specific examples thereof include a methoxy group, an ethoxy group, a n-propoxy group, an isopropoxy group, a n-butoxy group, a s-butoxy group, an isobutoxy group, a t-butoxy group, a n-pentyloxy group, a neopentyloxy group, a n-hexyloxy group, and the like.

Examples of the aryl group as the substituent include aryl groups having, for example, 6 to 14 carbon atoms, and specific examples thereof include a phenyl group, a naphthyl group, an anthryl group, a phenanthryl group, a biphenyl group, and the like.

Examples of the heterocyclic group as the substituent include aliphatic heterocyclic groups and aromatic heterocyclic groups. Examples of the aliphatic heterocyclic groups include 5- to 8-membered, preferably 5- or 6-membered, monocyclic, polycyclic, or fused polycyclic aliphatic heterocyclic groups which have, for example, 2 to 14 carbon atoms, and which contain, as their hetero atoms, at least one, preferably 1 to 3 hetero atoms such as nitrogen atoms, oxygen atoms, and sulfur atoms. Specific examples of the aliphatic heterocyclic groups include a 2-oxopyrrolidyl group, a piperidino group, a piperazinyl group, a morpholino group, a tetrahydrofuryl group, a tetrahydropyranyl group, a tetrahydrothienyl group, and the like. Meanwhile, examples of the aromatic heterocyclic groups include 5- to 8-membered, preferably 5- or 6-membered, monocyclic, polycyclic, or fused polycyclic aromatic heterocyclic (heteroaryl) groups which have, for example, 2 to 15 carbon atoms, and which contain, as their hetero atoms, at least one, preferably 1 to 3 hetero atoms such as nitrogen atoms, oxygen atoms, and sulfur atoms. Specific examples thereof include a furyl group, a thienyl group, a pyridyl group, a pyrimidinyl group, a pyrazinyl group, a pyridazinyl group, a pyrazolyl group, an imidazolyl group, an oxazolyl group, a thiazolyl group, a benzofuryl group, a benzothienyl group, a quinolyl group, an isoquinolyl group, a quinoxalyl group, a phthalazinyl group, a quinazolinyl group, a naphthyridinyl group, a cinnolinyl group, a benzoimidazolyl group, a benzoxazolyl group, a benzothiazolyl group, and the like.

When $R^1$ and $R^2$ and/or $R^3$ and $R^4$ are bonded to each other to form a ring, the ring formed by $R^1$ and $R^2$ and/or $R^3$ and $R^4$ together with the phosphorus atom to which the $R^1$ and $R^2$ and/or $R^3$ and $R^4$ are bonded may be a four-membered ring, a five-membered ring, or a six-membered ring. Specific examples of the ring include a phosphetane ring, a phospholane ring, a phosphorinane ring, a 2,4-dimethyl phosphetane ring, a 2,4-diethylphosphetane ring, a 2,5-dimethyl phospholane ring, a 2,5-diethylphospholane ring, a 2,6-dimethyl phosphorinane ring, a 2,6-diethylphosphorinane ring, and the like.

Examples of the alkylene chain represented by A in the general formula (1) include a methylene group, an ethylene group, a trimethylene group, a tetramethylene group, a pentamethylene group, a hexamethylene group, and the like.

Examples of the cycloalkanediyl group represented by A in the general formula (1) include cyclobutanediyl groups, cyclopentanediyl groups, cyclohexanediyl groups, cycloheptanediyl groups, and the like.

Examples of the alaryldiyl group represented by A in the general formula (1) include a toluene-2,α-diyl group, a 1,2-xylene-α,α'-diyl group, a 1,3-xylene-α,α'-diyl group, and the like.

Examples of the aryldiyl group represented by A in the general formula (1) include benzenediyl groups, naphthalenediyl groups, anthracenediyl groups, phenanthrenediyl groups, biphenyldiyl groups, binaphthyldiyl groups, 4,4'-bi(1,3-benzodioxole)diyl group, a ferrocenediyl group, and the like.

Each of the alkylene chain, the cycloalkanediyl group, the alaryldiyl group, and the aryldiyl group represented by A in the general formula (1) may have a substituent. Examples of the substituent include alkyl groups, alkoxy groups, aryl groups, heterocyclic groups, and the like.

Here, examples of the alkyl group as the substituent include linear or branched alkyl groups having, for example, 1 to 15 carbon atoms, preferably 1 to 10 carbon atoms, and more preferably 1 to 6 carbon atoms, and specific examples thereof include a methyl group, an ethyl group, a n-propyl group, an isopropyl group, a n-butyl group, a s-butyl group, an isobutyl group, a t-butyl group, a n-pentyl group, a neopentyl group, a n-hexyl group, and the like.

Examples of the alkoxy group as the substituent include linear or branched alkoxy groups having, for example, 1 to 6 carbon atoms, and specific examples thereof include a methoxy group, an ethoxy group, a n-propoxy group, an isopropoxy group, a n-butoxy group, a s-butoxy group, an isobutoxy group, a t-butoxy group, a n-pentyloxy group, a neopentyloxy group, a n-hexyloxy group, and the like.

Examples of the aryl group as the substituent include aryl groups having, for example, 6 to 14 carbon atoms, and specific examples thereof include a phenyl group, a naphthyl group, an anthryl group, a phenanthryl group, a biphenyl group, and the like.

Examples of the heterocyclic group as the substituent include aliphatic heterocyclic groups and aromatic heterocyclic groups. Examples of the aliphatic heterocyclic group include 5- to 8-membered, preferably 5- or 6-membered monocyclic, polycyclic, or fused polycyclic aliphatic heterocyclic groups which have, for example, 2 to 14 carbon atoms, and which contain, as their hetero atoms, at least one, preferably 1 to 3 hetero atoms such as nitrogen atom, oxygen atoms, and sulfur atoms. Specific examples of the aliphatic heterocyclic groups include a 2-oxopyrrolidyl group, a piperidino group, a piperazinyl group, a morpholino group, a tetrahydrofuryl group, a tetrahydropyranyl group, a tetrahydrothienyl group, and the like. Meanwhile examples of the aromatic heterocyclic groups include 5- to 8-membered, preferably 5- or 6-membered monocyclic, polycyclic, or fused polycyclic aromatic heterocyclic (heteroaryl) groups which have, for example, 2 to 15 carbon atoms, and which contain, as their hetero atoms, at least one, preferably 1 to 3 hetero atoms such as nitrogen atoms, oxygen atoms, and sulfur atoms. Specific examples thereof include a furyl group, a thienyl group, a pyridyl group, a pyrimidinyl group, a pyrazinyl group, a pyridazinyl group, a pyrazolyl group, an imidazolyl group, an oxazolyl group, a thiazolyl group, a benzofuryl group, a benzothienyl group, a quinolyl group, an isoquinolyl group, a quinoxalyl group, a phthalazinyl group, a quinazolinyl group, a naphthyridinyl group, a cinnolinyl group, a benzoimidazolyl group, a benzoxazolyl group, a benzothiazolyl group, and the like.

Specific examples of the diphosphine compound represented by the general formula (1) include bis(diphenylphosphino)methane, 1,2-bis(diphenylphosphino)ethane, 1,3-bis(diphenylphosphino)propane, 1,4-bis(diphenylphosphino)butane, 1,5-bis(diphenylphosphino)pentane, 1,6-bis(diphenylphosphino)hexane, 1,2-bis(diphenylphosphino)benzene, 1,2-bis(anisylphenylphosphino)ethane, 2,3-bis(diphenylphosphino)butane, 1,2-bis(diphenylphosphino)propane, 2,3-bis(diphenylphosphino)-5-norbornene, 2,3-O-isopropylidene-2,3-dihydroxy-1,4-bis(diphenylphosphino)butane, 1-cyclohexyl-1,2-bis(diphenylphosphino)ethane, 2,4-bis-(diphenylphosphino)pentane, 2,2'-bis(diphenylphosphino)-1,1'-bicyclopentane, 2,2'-bis(diphenylphosphino)-1,1'-binaphthyl, 2,2'-bis(diphenylphosphino)-1,1'-(5,5',6,6',7,7',8,8'-octahydrobinaphthyl), 2,2'-bis(di-p-tolylphosphino)-1,1'-binaphthyl, 2,2'-bis(di(3,5-dimethylphenyl)phosphino)-1,1'-binaphthyl, 2,2'-bis(diphenylphosphino)-6,6'-dimethyl-1,1'-biphenyl, (4,4'-bi-1,3-benzodioxole)-5,5'-diylbis(diphenylphosphine), (4,4'-bi-1,3-benzodioxole)-5,5'-diylbis

[bis(3,5-dimethylphenyl)phosphine], [(4S)-[4,4'-bi-1,3-benzodioxole]-5,5'-diyl]bis[bis[3,5-bis(1,1-dimethylethyl)-4-methoxyphenyl]phosphine], 2,2'-bis(diphenylphosphino)benzophenone, 2,2'-bis(di(3,5-dimethylphenyl)phosphino)benzophenone, and the like. These diphosphine compounds may be racemic or optically active.

The amount of the diphosphine compound used is 0.1 to 10 equivalent, preferably 1 to 5 equivalent to the copper atoms in the homogeneous copper catalyst.

The production method of the present invention can be suitably carried out without any solvent or in a solvent. However, it is preferable to use a solvent. The solvent used is preferably one capable of dissolving the hydrogenation substrate and the catalyst, and a single solvent or a mixture solvent is used. Specific examples thereof include aromatic hydrocarbons such as toluene and xylene; aliphatic hydrocarbons such as hexane and heptane; halogenated hydrocarbons such as methylene chloride and chlorobenzene; ethers such as diethyl ether, tetrahydrofuran, methyl t-butyl ether, and cyclopentyl methyl ether; alcohols such as methanol, ethanol, 1-propanol, 2-propanol, n-butanol, and 2-butanol; polyols such as ethylene glycol, propylene glycol, 1,2-propanediol, and glycerine; nitriles such as acetonitrile; amides such as N,N-dimethylformamide and N-methylpyrrolidone; amines such as pyridine and triethylamine; and the like. Of these, alcohols are preferable. Particularly preferable are ethanol, 1-propanol and 2-propanol. The amount of the solvent used can be selected as appropriate depending on reaction conditions and the like, and may be an amount with which the concentration of the raw material can be 0.05 mol/L to 8.0 mol/L, and preferably 0.8 mol/L to 3.0 mol/L. The reaction is performed with stirring, if necessary.

In a preferred embodiment of the production method of the present invention, a base can be further added to the reaction system, and thus the reaction can be performed in the presence of the base. This allows the hydrogenation reaction to proceed smoothly. Examples of the base used and added to the reaction system include organic base compounds and inorganic base compounds.

Specific examples of the above-described organic base compounds used in the present invention include amines such as triethylamine, diisopropylethylamine, N,N-dimethylaniline, piperidine, pyridine, 4-dimethylaminopyridine, 1,5-diazabicyclo[4.3.0]nona-5-ene, 1,8-diazabicyclo[5.4.0]undec-7-ene, tri-n-butylamine, and N-methylmorpholine. Of these, triethylamine, diisopropylethylamine, and the like are particularly preferable.

Examples of the inorganic base compounds used in the present invention include alkali metal carbonates such as potassium carbonate, sodium carbonate, lithium carbonate, and cesium carbonate; alkaline earth metal carbonates such as magnesium carbonate, and calcium carbonate; alkali metal hydrogen carbonates such as sodium hydrogen carbonate and potassium hydrogen carbonate; alkali metal hydroxides such as sodium hydroxide, potassium hydroxide, and lithium hydroxide; alkaline earth metal hydroxides such as magnesium hydroxide and calcium hydroxide; alkali metal alkoxides such as sodium methoxide, sodium ethoxide, sodium isopropoxide, sodium t-butoxide, potassium methoxide, potassium ethoxide, potassium isopropoxide, potassium t-butoxide, lithium methoxide, lithium isopropoxide, and lithium t-butoxide; alkaline earth metal alkoxides such as magnesium methoxide and magnesium ethoxide; and metal hydrides such as sodium hydride and calcium hydride. Of these, particularly preferable are sodium carbonate, potassium carbonate, cesium carbonate, sodium t-butoxide, potassium t-butoxide, sodium hydroxide, potassium hydroxide, and lithium hydroxide.

In the present invention, the amount of the base compound used can be selected as appropriate depending on the catalyst used, reaction conditions, and the like, and is generally 0.1 equivalent to 1,000 equivalent, and preferably 1 equivalent to 100 equivalent relative to the homogeneous copper catalyst. Note that the base compound can be added, as it is, to the reaction system, or can be added to the reaction system as a solution in which the base compound is dissolved in the reaction solvent or the like.

In the present invention, it is also possible to mix one or both of the diphosphine compound and the base with the homogeneous copper catalyst in advance, and then use the mixture as the catalyst. Specifically, the diphosphine compound and/or the base are mixed with the homogeneous copper catalyst in a solvent in advance, and stirring is performed. Then, the residue obtained by evaporating the solvent is added to the reaction system as the catalyst. Alternatively, the residue is dissolved in a solvent, and then the obtained solution is added to the reaction as the catalyst. This may lead to improvement in the conversion of the hydrogenation substrate into the alcohol, and improvement in selectivity which means the conversion into the desired alcohol.

Moreover, in a preferred embodiment of the production method of the present invention, it is possible to perform the production method in the presence of an additive such as an ammonium salt or a phosphonium salt.

Specific examples of the ammonium salt include ammonium chloride, tetrabutylammonium chloride, tetrabutylammonium bromide, tetrabutylammonium fluoride, tetraphenylammonium chloride, and the like.

Specific examples of the phosphonium salt include tetraphenylphosphonium chloride, tetraphenylphosphonium bromide, and the like.

The amount of the additive used is 0 to 10 equivalent, and preferably 0.0001 to 2 equivalent, with respect to the substrate.

Moreover, in a preferred embodiment of the production method of the present invention, it is possible to perform the production method while a monophosphine compound represented by the general formula (5) is further added.

The amount of the monophosphine added is generally 0 to 20 equivalent, and preferably 0 to 10 equivalent, with respect to the homogeneous copper catalyst.

In the present invention, the reaction temperature for performing the hydrogenation reaction is preferably 0° C. to 150° C., and more preferably 20° C. to 100° C. If the reaction temperature is too low, a large amount of an unreacted raw material may remain. Meanwhile, if the reaction temperature is too high, the raw material, the catalyst, or the like may decompose. Hence, both cases are not preferable.

In the present invention, the hydrogen pressure for performing the hydrogenation reaction is preferably 0.1 MPa to 10 MPa, and more preferably 0.5 MPa to 6 MPa.

Meanwhile, the reaction time is generally about 1 hour to 100 hours, and preferably 5 hours to 24 hours, in which a sufficiently high raw-material conversion can be achieved. After the reaction is completed, a desired alcohol compound can be obtained by one of generally used purification methods such as extraction, filtration, crystallization, distillation, and various kinds of chromatography, or by an appropriate combination thereof.

EXAMPLES

The present invention will be described in detail on the basis of Examples shown below. However, the present invention is not limited to these Examples at all. Note that the conversion and the selectivity were determined by gas chromatography (GC). The apparatus used and measurement conditions were as follows:

GC: GC353B (manufactured by GL Sciences Inc.)
Column: BC-WAX 0.25 mm (I.D.)×30 m (length), 0.250 μm (thickness) [manufactured by GL Sciences Inc.]
Conditions: injection 220° C., detector 250° C.
Column initial temperature: 50° C. (10 min.), Rate of temperature rise of column: 10° C./min., Column final temperature: 230° C. (32 min.)
Note that DPPB represents 1,4-bis (diphenylphosphino) butane.
Meanwhile, S/C represents a molar ratio of the hydrogenation substrate to the catalyst.

Examples 1 to 6

Hydrogenation Reactions of α,β-Unsaturated Aldehydes (S/C=500)

Into a stainless steel autoclave equipped with a glass inner tube, [Cu (NO$_3$) (PPh$_3$)$_2$] (11.7 mg, 0.018 mmol) and DPPB (7.7 mg, 0.018 mmol) were introduced. The inside of the autoclave was then replaced with nitrogen. To the autoclave, an ethanolic solution of sodium hydroxide (0.03 M) (6.0 mL, 0.18 mmol) and each α,β-unsaturated aldehyde (9 mmol) were added, and stirring was performed at a hydrogen pressure of 5 MPa at 50° C. for 16 hours. The hydrogen was released with great care, and the conversion was analyzed by GC. The contents were concentrated, and then purified by silica gel chromatography. Thus, the corresponding alcohol was obtained. Table 1 shows the substrates, the conversions, and the isolated yields.

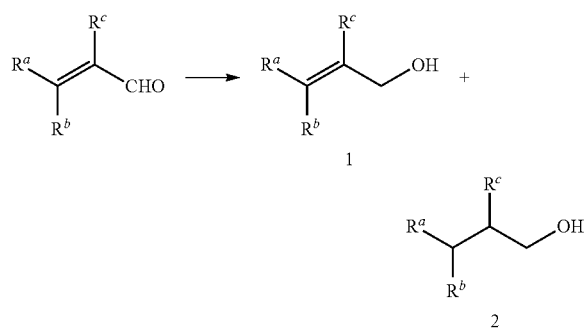

Example 7

Hydrogenation Reaction of α-Methyl Cinnamic Aldehyde (S/C=1000)

Into a stainless steel autoclave equipped with a glass inner tube, [Cu(NO$_3$)(PPh$_3$)$_2$] (11.7 mg, 0.018 mmol) and DPPB (7.7 mg, 0.018 mmol) were introduced. The inside of the autoclave was then replaced with nitrogen. To the autoclave, an ethanolic solution of sodium hydroxide (0.03 M) (6.0 mL, 0.18 mmol), 6 mL of ethanol, and a-methyl cinnamic aldehyde (E/Z=99/1; 2.52 mL, 18 mmol) were added, and stirring was performed at a hydrogen pressure of 5 MPa at 50° C. for 16 hours. The hydrogen was released with great care, and the conversion was analyzed by GC. The conversion was 98%. The contents were concentrated, and then purified by silica gel chromatography. Thus, 2.53 g of the corresponding alcohol was obtained.

Isolated yield: 95%, E/Z(1b)=99/1, 1b/2b=>99/1

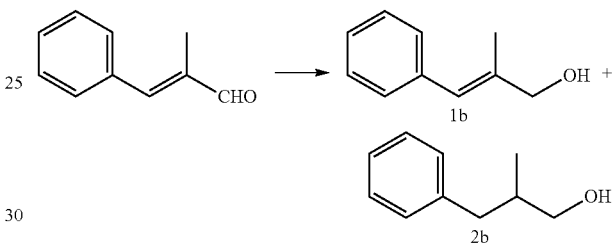

Example 8

Hydrogenation Reaction of α-Methyl Cinnamic Aldehyde (Using Cu(NO$_3$)$_2$.3H$_2$O and PPh$_3$)

Into a stainless steel autoclave equipped with a glass inner tube, Cu(NO$_3$)$_2$.3H$_2$O (3.4 mg, 0.018 mmol), triphenylphosphine (14.2 mg, 0.054 mmol), and DPPB (7.7 mg, 0.018 mmol) were introduced. The inside of the autoclave was then replaced with nitrogen. To the autoclave, an ethanolic solution of sodium hydroxide (0.03 M) (6.0 mL, 0.18 mmol), 6 mL of ethanol, and α-methyl cinnamic aldehyde (E/Z=99/1; 1.26 mL, 9 mmol) were added, and stirring was performed at a hydrogen pressure of 5 MPa at 50° C. for 16 hours. The hydrogen was released with great care, and the conversion was analyzed by GC. The conversion was 99%. The contents were concentrated, and then purified by silica gel chromatography. Thus, the corresponding alcohol was obtained.

Isolated yield: 97%, E/Z(1b)=99/1, 1b/2b=>99/1

TABLE 1

| Example | $R^a$ | $R^b$ | $R^c$ | E/Z (hydrogenation substrate) | Conversion (%) | Isolated yield (%) | E/Z of 1 | 1/2 |
|---|---|---|---|---|---|---|---|---|
| 1 | Ph | H | Me | 99/1 | >99 | 99 | 99/1 | >99/1 |
| 2 | Ph | H | n-Amyl | 95/5 | >99 | 98 | 95/5 | >99/1 |
| 3 | Ph | Ph | H | N.A. | 98 | 96 | N.A. | >99/1 |
| 4 | Ph | H | H | >99/1 | >99 | 68 | >99/1 | >99/1 |
| 5 | n-Pr | H | Et | 94/6 | 98 | 87 | 91/9 | 16/1 |
| 6 | Et | H | Me | 99/1 | >99 | 72 | 97/3 | 40/1 |

Example 9

Hydrogenation Reaction of α-Methyl Cinnamic Aldehyde (Using Cu (NO$_3$)$_2$.3H$_2$O)

Into a stainless steel autoclave equipped with a glass inner tube, Cu (NO$_3$)$_2$ (3.4 mg, 0.018 mmol) and DPPB (7.7 mg, 0.018 mmol) were introduced. The inside of the autoclave was then replaced with nitrogen. To the autoclave, an ethanolic solution of sodium hydroxide (0.03 M) (6.0 mL, 0.18 mmol) and α-methyl cinnamic aldehyde (E/Z=99/1; 1.26 mL, 9 mmol) were added, and stirring was performed at a hydrogen pressure of 5 MPa at 50° C. for 16 hours. The hydrogen was released with great care, and the conversion was analyzed by GC. The conversion was 99%. The contents were concentrated, and then purified by silica gel chromatography. Thus, the corresponding alcohol was obtained.

Isolated yield: 91%, E/Z(1b)=99/1, 1b/2b=>99/1

Example 10

Hydrogenation Reaction of α-Methyl Cinnamic Aldehyde (Using n-Butanol Solvent)

Into a stainless steel autoclave equipped with a glass inner tube, [Cu (NO$_3$) (PPh$_3$)$_2$] (11.7 mg, 0.018 mmol) and DPPB (7.7 mg, 0.018 mmol) were introduced. The inside of the autoclave was then replaced with nitrogen. To the autoclave, a n-butanol solution of sodium hydroxide (0.03 M) (6.0 mL, 0.18 mmol) and α-methyl cinnamic aldehyde (E/Z=99/1; 1.26 mL, 9 mmol) were added, and stirring was performed at a hydrogen pressure of 5 MPa at 50° C. for 16 hours. The hydrogen was released with great care, and the conversion was analyzed by GC. The conversion was 99%.

Example 11

Hydrogenation Reaction of α-Methyl Cinnamic Aldehyde (Using tert-Butanol Solvent)

Into a stainless steel autoclave equipped with a glass inner tube, [Cu(NO$_3$) (PPh$_3$)$_2$](11.7 mg, 0.018 mmol) and DPPB (7.7 mg, 0.018 mmol) were introduced. The inside of the autoclave was then replaced with nitrogen. To this autoclave, a tert-butanol solution of sodium hydroxide (0.03 M) (6.0 mL, 0.18 mmol) and α-methyl cinnamic aldehyde (9 mmol) were added, and stirring was performed at a hydrogen pressure of 5 MPa at 50° C. for 16 hours. The hydrogen was released with great care, and the conversion was analyzed by GC. The conversion was 99%.

Example 12

Hydrogenation Reaction of 2-Ethyl-4-(2,2,3-trimethylcyclopento-3-ene-1-yl)-2-buten-1-al Into a stainless steel autoclave equipped with a glass inner tube, [Cu (NO$_3$) (PPh$_3$)$_2$] (11.7 mg, 0.018 mmol) and DPPB (7.7 mg, 0.018 mmol) were introduced. The inside of the autoclave was then replaced with nitrogen. To the autoclave, an ethanolic solution of sodium hydroxide (0.03 M) (6.0 mL, 0.18 mmol) and 2-ethyl-4-(2,2,3-trimethylcyclopento-3-ene-1-yl)-2-buten-1-al (E/Z=93/7; 2.02 mL, 9 mmol) were added, and stirring was performed at a hydrogen pressure of 5 MPa at 50° C. for 16 hours. The hydrogen was released with great care, and the conversion was analyzed by GC. The conversion was 98%. The contents were concentrated, and then purified by silica gel chromatography. Thus, 1.76 g of the corresponding alcohol was obtained.

Isolated yield: 94%, E/Z(1c)=96/4, 1c/2c=35/1

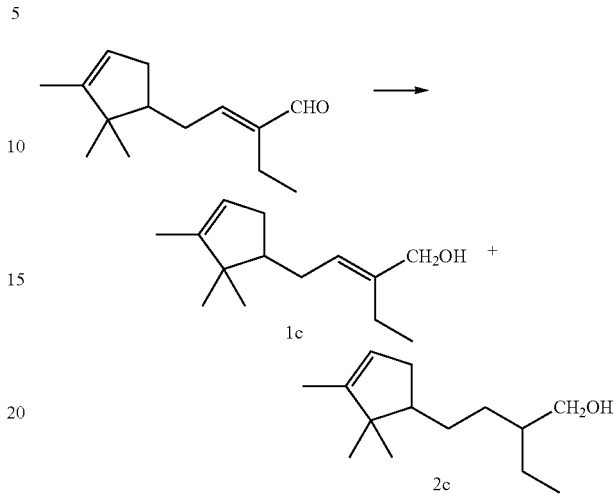

Example 13

Hydrogenation Reaction of Perillaldehyde (S/C=500)

Into a stainless steel autoclave equipped with a glass inner tube, [Cu(NO$_3$)(PPh$_3$)$_2$] (11.7 mg, 0.018 mmol) and DPPB (7.7 mg, 0.018 mmol) were introduced. The inside of the autoclave was then replaced with nitrogen. To the autoclave, an ethanolic solution of sodium hydroxide (0.03 M) (6.0 mL, 0.18 mmol) and perillaldehyde (2.02 mL, 9 mmol) were added, and stirring was performed at a hydrogen pressure of 5 MPa at 50° C. for 16 hours. The hydrogen was released with great care, and the conversion was analyzed by GC (>99%). The contents were concentrated, and then purified by silica gel chromatography. Thus, 1.26 g of the corresponding alcohol was obtained.

Isolated yield: 92%, 1d/2d=52/1

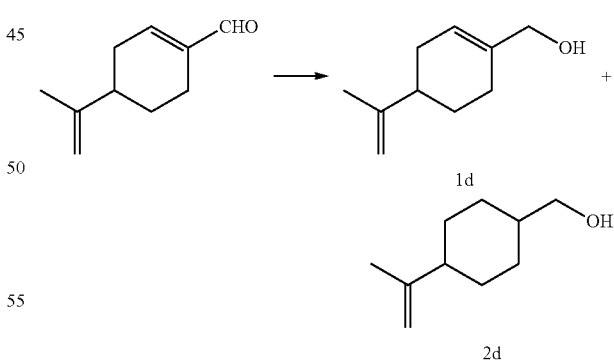

Comparative Example 1

Hydrogenation Reaction of Perillaldehyde (in accordance with the Method in Non-Patent Document 4; Amount of Catalyst Used: 0.2 mol %)

Into a stainless steel autoclave equipped with a glass inner tube, [CuH(PPh$_3$)]$_6$ (16.3 mg, 0.05 mmol; in terms of Cu) was introduced. The inside of the autoclave was then replaced with nitrogen. To this autoclave, toluene (17.0 mL), tert-butyl alcohol (0.19 mL, 2.0 mmol), dimethylphenylphosphine (43 µl, 0.3 mmol), and perillaldehyde (3.89 mL, 25 mmol) were added, and stirring was performed at a hydrogen pressure of 5 MPa at 30° C. for 16 hours. The hydrogen was released with great care, and the conversion was analyzed by GC. The conversion was less than 1%.

Example 14

Hydrogenation Reaction of 3-(2-Furyl)-acrolein

Into a stainless steel autoclave equipped with a glass inner tube, [Cu(NO$_3$)(PPh$_3$)$_2$] (11.7 mg, 0.018 mmol), DPPB (7.7 mg, 0.018 mmol) and 3-(2-furyl)-acrolein (E/Z=>99/1, 1.24 g, 9 mmol) were introduced. The inside of the autoclave was then replaced with nitrogen. To the autoclave, an ethanolic solution of sodium hydroxide (0.03 M) (6.0 mL, 0.18 mmol) was added, and stirring was performed at a hydrogen pressure of 5 MPa at 50° C. for 16 hours. The hydrogen was released with great care, and the conversion was analyzed by GC (>99%). The contents were concentrated, and then purified by silica gel chromatography. Thus, 1.15 g of the corresponding alcohol was obtained.

Isolated yield: 91%, E/Z(1e)=>99/1, 1e/2e=>99/1

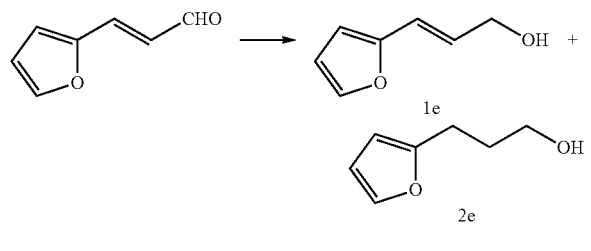

Example 15

Hydrogenation Reaction of 3-(2-Furyl)-acrolein (with [CuH(PPh$_3$)]$_6$)

Into a stainless steel autoclave equipped with a glass inner tube, [CuH(PPh$_3$)]$_6$ (5.9 mg, 0.018 mmol; in terms of Cu), DPPB (7.7 mg, 0.018 mmol) and 3-(2-furyl)-acrolein (E/Z=>99/1, 1.24 g, 9 mmol) were introduced. The inside of the autoclave was then replaced with nitrogen. To the autoclave, an ethanolic solution of sodium hydroxide (0.03 M) (6.0 mL, 0.18 mmol) was added, and stirring was performed at a hydrogen pressure of 5 MPa at 50° C. for 15 hours. The hydrogen was released with great care, and the conversion was analyzed by GC (>99%). The contents were concentrated, and then purified by silica gel chromatography. Thus, 1.21 g of the corresponding alcohol was obtained.

Isolated yield: 96%, E/Z(1e)=>99/1, 1e/2e=>99/1

Examples 16 to 23

Hydrogenation Reactions of Aldehydes

Into a stainless steel autoclave equipped with a glass inner tube, [Cu (NO$_3$) (PPh$_3$)$_2$] (11.7 mg, 0.018 mmol) and DPPB (7.7 mg, 0.018 mmol) were introduced. The inside of the autoclave was then replaced with nitrogen. To the autoclave, an ethanolic solution of sodium hydroxide (0.03 M) (6.0 mL, 0.18 mmol) and each aldehyde (9 mmol) were added, and stirring was performed at a hydrogen pressure of 5 MPa at 50° C. for 16 hours. The hydrogen was released with great care, and the conversion was analyzed by GC. The contents were concentrated, and then purified by silica gel chromatography. Thus, the corresponding alcohol was obtained. Table 2 shows the substrates, the conversions, and the isolated yields.

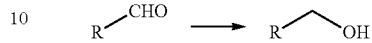

TABLE 2

| Example | R | Conversion (%) | Isolated yield (%) |
|---|---|---|---|
| 16 | Ph | >99 | 91 |
| 17 | 3,4-Methylenedioxyphenyl | >99 | 98 |
| 18 | 2-(5-Methylfuryl) | >99 | 87 |
| 19 | 2-Thienyl | >99 | 96 |
| 20 | 3-Pyridyl | >99 | 85 |
| 21 | 1-Phenylethyl | >99 | 76 |
| 22 | 2-Phenylethyl | 88 | 10 |
| 23 | cyclohexyl | >99 | 90 |

The invention claimed is:

1. A method for producing an alcohol compound, said method comprising performing a hydrogenation reaction of an aldehyde compound of the following general formula (3):

wherein $R^5$ to $R^7$ each independently represent a hydrogen atom, an alkyl group which has 1 to 10 carbon atoms and which may have a substituent, an alkenyl group which may have a substituent, an alicyclic group which has 5 to 8 carbon atoms and which may have a substituent, an aryl group which may have a substituent, or a heterocyclic group which may have a substituent; and $R^5$ and $R^6$ and/or $R^5$ and $R^7$, may be bonded to each other to form a ring, in the presence of a homogeneous copper catalyst and a diphosphine compound of the following general formula (1):

wherein $R^1$ to $R^4$ each independently represent an alkyl group having 1 to 10 carbon atoms, an alicyclic group which has 5 to 8 carbon atoms and which may have a substituent, an aryl group which may have a substituent, or a heterocyclic group which may have a substituent; $R^1$ and $R^2$ and/or $R^3$ and $R^4$, may be bonded to each other to form a ring; and A represents an alkylene chain which may have a substituent, a cycloalkanediyl group which may have a substituent, an alaryldiyl group which may have a substituent, or an aryldiyl group which may have a substituent.

2. The production method according to claim 1, wherein the hydrogenation reaction of the aldehyde compound is performed in the presence of the homogeneous copper catalyst, the diphosphine compound, and an alcohol.

\* \* \* \* \*